US006500862B1

(12) United States Patent
Zanello

(10) Patent No.: US 6,500,862 B1
(45) Date of Patent: Dec. 31, 2002

(54) STABLE MICROEMULSIONS FOR THE ADMINISTRATION OF FATTY ACIDS TO HUMANS OR TO ANIMALS, AND USE OF THESE MICROEMULSIONS

(75) Inventor: Philippe Zanello, Begles (FR)

(73) Assignee: Ceva Sante Animale, Libourne (FR)

( * ) Notice: Subject to any disclaimer, the term of this patent is extended or adjusted under 35 U.S.C. 154(b) by 0 days.

(21) Appl. No.: 09/610,374

(22) Filed: Jul. 5, 2000

(30) Foreign Application Priority Data

Jul. 5, 1999 (FR) ............................................ 99 08653

(51) Int. Cl.⁷ .......................... A01N 37/00; A61K 9/12; B01F 17/00; C07C 53/00
(52) U.S. Cl. ........................... 514/558; 424/45; 516/58; 554/1; 554/2; 562/606
(58) Field of Search .................. 424/70.2, 45; 514/558; 516/58; 554/1, 2; 562/606

(56) References Cited

U.S. PATENT DOCUMENTS

| | | | | |
|---|---|---|---|---|
| 4,559,162 A | * | 12/1985 | Abel et al. .................. | 252/321 |
| 5,250,236 A | * | 10/1993 | Gasco ........................ | 264/4.4 |
| 5,709,863 A | * | 1/1998 | Pageat .................... | 424/195.11 |
| 6,071,975 A | * | 6/2000 | Halloran ...................... | 516/58 |

FOREIGN PATENT DOCUMENTS

| | | |
|---|---|---|
| EP | 0526666 A | 2/1993 |
| EP | 0608828 A | 8/1994 |
| WO | WO-9709964 * | 9/1995 |

* cited by examiner

*Primary Examiner*—Jose' G. Dees
*Assistant Examiner*—Mina Haghighatian
(74) *Attorney, Agent, or Firm*—Jacobson Holman PLLC

(57) ABSTRACT

The present invention relates to a stable, nondetergent composition based on fatty acids, in microemulsion form, for administration to humans or animals, comprising:

- from 5 to 30% by weight of one or more fatty acids with a free carboxylic acid function, as active ingredient;
- from 5 to 35% by weight of one or more surfactants;
- from 5 to 30% by weight of one or more $C_1$–$C_{12}$ alcohols, as cosurfactant;
- from 5 to 35% by weight of one or more water-soluble compounds with a carbonyl or hydroxyl function; and
- from 0 to 35% by weight of one or more water-immiscible compounds;

the said composition having a pH of less than 6.5.

24 Claims, No Drawings

STABLE MICROEMULSIONS FOR THE ADMINISTRATION OF FATTY ACIDS TO HUMANS OR TO ANIMALS, AND USE OF THESE MICROEMULSIONS

The present invention relates to stable microemulsions for the administration of fatty acids to humans or to animals. These microemulsions, with a pH of less than 6.5, have a very high fatty acid concentration since they contain from 5 to 30% by weight of fatty acids.

The influence of fatty acids and of mixtures thereof on the behaviour of animals has been described and commented on in the literature. By way of illustration, there may be mentioned pheromones which may contain or constitute such mixtures of fatty acids.

Compositions based on fatty acids are more particularly known which have a soothing and relaxing effect on certain mammals. These compositions are capable of combating anxiety in an animal experiencing a particular stress situation caused for example by a change in its environment which is too sudden. U.S. Pat. No. 5,709,863 describes in particular fatty acid compositions which, simply upon bringing into contact with the olfactory organs of the respiratory tract, facilitate the adaptation of cats to an unknown environment by limiting their anxiety.

The emulsions described in U.S. Pat. No. 5,709,863 have, nevertheless, a number of disadvantages.

They are not easily dispersible in the environment because of their high viscosity.

Furthermore, they exhibit inadequate heat stability; it has been possible to observe crystallization of the fatty acids at low temperature and sometimes even at room temperature.

One way of reducing the viscosity of fatty acid compositions is to formulate these fatty acids in a microemulsion.

However, the formulation of microemulsions with high fatty acid concentrations, which are both chemically and heat stable, is problematic.

In fact, because of the high fatty acid concentrations (greater than 5% by weight), the use of cosurfactants such as alcohols is necessary. However, the simultaneous presence of alcohols and fatty acids in the microemulsions is a priori not desirable given the high risks of esterification. The chemical stability of such microemulsions appears compromised.

Surprisingly, the inventors have been able to develop a stable composition, in microemulsion form, comprising a high concentration of fatty acids and which may include up to 30% by weight of alcohol.

More precisely, the invention relates to a stable, nondetergent composition, in microemulsion form, for administration to humans or animals, comprising:
- from 5 to 30% by weight of one or more fatty acids with a free carboxylic acid function, as active ingredient;
- from 5 to 35% by weight of one or more surfactants;
- from 5 to 30% by weight of one or more $C_1$–$C_{12}$ alcohols, as cosurfactant;
- from 5 to 35% by weight of one or more water-soluble compounds with a carbonyl or hydroxyl function; and
- from 0 to 35% by weight of one or more water-immiscible compounds; the said composition having a pH of less than 6.5.

Fatty acid is understood to mean, according to the invention, saturated or unsaturated, linear or branched hydrocarbon chain-containing monocarboxylic acids which are active in humans or animals when administered thereto, this being regardless of the route of administration. More precisely, these fatty acids are chemical substances capable of modifying the behaviour or the physiological responses of humans or animals.

Usually, the fatty acids are in the form of $C_4$–$C_{22}$. Examples thereof are capric, lauric, myristic, palmitic, palmitoleic, oleic, linoleic, stearic, arachidonic, n-butyric, isobutyric, α-methylbutyric, caproic, pivalic, gamma-linoleic, eicosapentanoic and docosahexanoic acids.

At room temperature, these fatty acids are present either in liquid form or in solid form, depending on the length and structure of the carbon chain.

Examples of mixtures of fatty acids which can be used as active ingredient in the context of the invention are pheromones.

Preferably, the compositions of the invention comprise one of the following fatty acid mixtures:
- i—a mixture of oleic acid and palmitic acid;
- ii—a mixture of oleic acid and n-butyric acid;
- iii—a mixture of oleic acid, palmitic acid and linoleic acid;
- iv—a mixture of oleic acid, palmitic acid, linoleic acid and palmitoleic acid;
- v—a mixture of capric acid, lauric acid, myristic acid, palmitoleic acid, palmitic acid, linoleic acid and oleic acid;
- vi—a mixture of oleic acid, palmitic acid, linoleic acid and myristic acid;
- vii—a mixture of oleic acid, palmitic acid, linoleic acid, lauric acid and myristic acid;
- viii—a mixture of oleic acid, palmitic acid, linoleic acid, myristic acid and pentadecanoic acid;
- ix—a mixture of oleic acid, palmitic acid, linoleic acid, myristic acid, pentadecanoic acid and stearic acid;
- x—a mixture of oleic acid, palmitic acid, linoleic acid, myristic acid, lauric acid and pentadecanoic acid;
- xi—one of the $C_4$–$C_{22}$ fatty acid mixtures described in U.S. Pat. No. 5,709,863.

The composition of the invention preferably comprises from 10 to 30% by weight of one or more fatty acids, better still from 15 to 25% by weight, for example from 17 to 23% by weight.

According to the invention, it is essential that pH of the composition is less than 6.5. Preferably, the pH of this composition is between 3 and 6.

According to the invention, the composition in microemulsion form may comprise one or more surfactants chosen from an anionic, cationic, zwitterionic or nonionic surfactant as long as its nature is not incompatible with its use.

Preferably, the compositions of the invention comprise exclusively pharmaceutically acceptable constituents.

Thus, the preferred surfactants are anionic, and better still nonionic, surfactants.

Examples of anionic surfactants which may be suitable are alkyl sulphates in which the alkyl chain is $C_6$–$C_{18}$, such as sodium lauryl sulphate, alkyl benzenesulphonates in which the alkyl chain is $C_6$–$C_{18}$ and dialkyl sulphosuccinates in which the alkyl chain is $C_6$–$C_{18}$, such as sodium dioctyl sulphosuccinate.

The counter-ion for the alkyl sulphates, for the alkyl benzenesulphonates and for the dialkyl sulphosuccinates is preferably the cation of an alkali metal such as sodium or potassium, or alternatively an ammonium cation.

Examples of nonionic surfactants are:
a) the product of condensation of an aliphatic fatty alcohol, preferably a $C_8$–$C_{22}$, with a $C_2$–$C_3$ alkylene oxide. The $C_2$–$C_3$ alkylene oxide may be ethylene oxide, propylene oxide or alternatively a mixture of ethylene oxide and propylene oxide in any proportions. An example of such surfactants is the product of condensation of lauryl alcohol (or n-dodecyl alcohol) with 30 mol of ethylene oxide;

b) the product of condensation of an alkylphenol in which the alkyl chain is $C_8$–$C_{22}$ with a $C_2$–$C_3$ alkylene oxide. Here again, the products of condensation with ethylene oxide, propylene oxide or alternatively a mixture of ethylene oxide and propylene oxide in any proportions are also advantageous. By way of example of such surfactants, there may be mentioned the product of condensation of n-nonylphenol with 10 mol of ethylene oxide;

c) the product of condensation of a fatty acid, preferably a $C_8$–$C_{22}$, with a $C_2$–$C_3$ alkylene oxide, for example ethylene oxide or propylene oxide or a mixture of ethylene oxide and propylene oxide in any proportions. These condensation products contain a chain alkoxylated at the level of the hydroxyl function of the carboxyl group. Preferred surfactants of this group are the condensation products obtained from oleic acid, palmitic acid and stearic acid;

d) the product of condensation of a $C_8$–$C_{22}$ fatty acid glyceride with a $C_2$–$C_3$ alkylene oxide such as ethylene oxide and/or propylene oxide. Among these, ethoxylated glyceryl palmitate is preferred;

e) the product of condensation of a $C_8$–$C_{22}$ fatty acid ester of sorbitol with a $C_2$–$C_3$ alkylene oxide which may be ethylene oxide, propylene oxide or mixtures thereof. These compounds are polysorbates. A preferred example is sold under the name Tween 80;

f) the product of condensation of sorbitol with a $C_8$–$C_{22}$ fatty acid.

As surfactant, it is preferred to use either an alkali metal alkyl sulphate or a nonionic surfactant of the c) type or of the e) type above.

According to the invention, it is possible to envisage the combination of one or more surfactants.

Thus, particularly advantageous combinations of surfactants are the combination:

of a nonionic surfactant of the e) type with a nonionic surfactant of the f) type;

of an anionic surfactant such as a dialkyl sulphosuccinate with a nonionic surfactant of the e) type or of the f) type;

of an anionic surfactant such as an alkyl sulphate with a nonionic surfactant of the e) type or of the f) type.

Preferably, the composition of the invention comprises from 8 to 30% by weight of surfactant, better still from 10 to 30% by weight, for example from 10 to 25% by weight.

The composition of the invention comprises one or more linear or branched $C_1$–$C_{12}$ alcohols as cosurfactant. Preferably, these constituents represent from 5 to 25% by weight of the composition, better still from 10 to 20% by weight.

The alcohols of this type which can be used according to the invention are those generally used in the technology of microemulsions. Reference may be made for example to the book by Bourrel M. & Schechter R. S. entitled "Microemulsions are related systems" published by Marcel Dekker Inc., New York and Basle, 1988.

Preferred cosurfactants are aliphatic monohydroxylated alcohols and more particularly $C_1$–$C_4$ alkanols, such as isopropanol and ethanol.

The water-soluble compounds with a carbonyl or hydroxyl function have the effect of stabilizing the microemulsion of the invention from the chemical point of view. They are not surfactants. The exact nature of these compounds is unimportant as long as they comprise at least one carbonyl function or at least one hydroxyl function, it being possible for the latter to be the carbonyl or hydroxyl function of a carboxyl group.

It should be understood according to the invention that the water-soluble compound may comprise both a hydroxyl function and a carbonyl function.

A preferred group of such water-soluble compounds consists of glycols and their corresponding $C_1$–$C_4$ alkyl ethers.

In the context of the invention, the expression glycol denotes any compound corresponding to the formula HO-A-OH in which A represents an alkylene chain optionally interrupted by one or more oxygen atoms, the said alkylene chain being linear or branched, but preferably linear.

The alkylene chain may comprise from 2 to 100 carbon atoms and up to 50 oxygen atoms.

Examples of glycols are ethylene glycol, propylene glycol, diethylene glycol and polyethylene glycols.

The polyethylene glycols preferably used in the context of the invention have a molar mass of less than or equal to 2000.

The $C_1$–$C_4$ alkyl monoethers of these glycols are also preferred water-soluble compounds. Alkyl is understood according to the invention to mean saturated, linear or branched, aliphatic hydrocarbon groups such as methyl, ethyl, propyl, isopropyl, butyl, isobutyl and tert-butyl.

Other preferred water-soluble compounds are monosaccharides or disaccharides of the sorbitol, glucose, galactose, lactose, mannitol, xylitol, lactol, lyxose, arabinose, idose, mannose, fructose, xylose, altrose, erythrose, threose, fucose, rhamnose, ribose and sorbose type.

There may also be mentioned glycerol, alkyl monoethers and diethers of glycerol in which the alkyl portions are $C_1$–$C_4$, N-methylpyrrolidone, N-methylacetamide, N,N-dimethylacetamide and acetone.

Preferably, the composition comprises one or more water-soluble compounds chosen from N-methylacetamide, N,N-dimethylacetamide, N-methylpyrrolidone, a glycol optionally in $C_1$–$C_4$ alkyl monoether form, a monosaccharide, a disaccharide or glycerol. The glycols and their ethers as well as N-methylpyrrolidone are particularly preferred.

The content of water-soluble compounds with a carbonyl or hydroxyl function varies between 5 and 35% by weight of the composition, preferably between 10 and 30%, better still between 15 and 30%.

The microemulsion of the invention may comprise, in addition, one or more water-immiscible lipophilic compounds whose nature is not very critical as long as these compounds are chemically inert towards the other constituents of the composition. The compounds lack surfactant properties.

According to a preferred embodiment, the lipophilic compound is chosen from paraffins and isoparaffins, preferably saturated $C_5$–$C_{16}$ hydrocarbons, esters of $C_4$–$C_{20}$ fatty acid with a variety of alcohols and, for example, with glycerol or ($C_4$–$C_{20}$)alkylpyrrolidones. The esters of fatty acids with glycerol include the monoglycerides of fatty acids, the diglycerides of fatty acids and the triglycerides of fatty acids.

An example of alkylpyrrolidone is octylpyrrolidone.

The presence of one or more lipophilic constituents enhances the physical stability of the microemulsion.

When they are present, these constituents preferably represent from 5 to 35% of the total weight of the microemulsion, better still from 8 to 20% of the total weight of the microemulsion.

The microemulsions of the invention may comprise, in addition, antimicrobial preservatives such as a paraben ester or benzyl alcohol, or alternatively antioxidants chosen from gallic acid esters (such as propyl gallate), ethoxyquin, vitamin E, butylated hydroxyanisole, butylated hydroxytoluene and diphenylamine.

The microemulsions of the invention are prepared simply by mixing the constituents in any order. It is preferable, however, to prepare a premix from the fatty acids, the water-immiscible compounds and the water-soluble compounds, and then to add to this premix the surfactants, the cosurfactants and the water. According to the invention, the microemulsions are of the oil-in-water type.

They preferably comprise from 5 to 80% by weight of water, better still from 15 to 25% by weight.

The size of the droplets of the microemulsions varies generally from 0.01 to 0.1 $\mu$m. Because of the small size of the droplets, the microemulsions are translucent and not opaque.

The advantageous properties of the microemulsions of the invention are in particular:
   a good chemical stability: the fatty acids do not react with the cosurfactant alcohols of the composition;
   a good physical stability: the compositions of the invention remain clear, without any agglomeration of the droplets or phase separation being observed; and
   the microemulsions of the invention have a low viscosity, this being for a broad range of temperatures, and in particular of between 0 and 40° C.

The microemulsions of the invention are administerable to humans and to animals by the oral, sublingual, intravenous, transdermal, intramuscular, topical, subcutaneous or rectal route or even by simply bringing the active ingredient of the microemulsion of the invention, in liquid or vapour form, into contact with the olfactory organs situated at the inlet of the respiratory tracts.

Thus, the administration may be carried out by spraying, nebulization or atomization of the microemulsions into the environment around humans or animals or evaporation of the active ingredient after application of the microemulsion into this environment, via the natural respiratory mechanisms in humans or animals, or alternatively the administration may be carried out by inhalation.

The appropriate mode of administration depends on the nature of the constituents of the microemulsion and in particular on the nature of the fatty acids incorporated into it.

When the microemulsion contains fatty acids capable of modifying the behaviour or the physiological responses in humans or animals as active ingredient, administration simply by spraying, nebulization, atomization or application of the composition into the environment around humans or animals is perfectly appropriate.

The administered doses depend on the mode of administration, the nature of the active ingredients, the seriousness of the condition or pathology and the weight of the animal and/or the nature of the behaviour or of the physiological response desired.

Thus, according to another of its aspects, the invention relates to the use of compositions of the invention for modifying the behaviour of humans or animals without a therapeutic or prophylactic treatment being involved.

According to yet another of its aspects, the invention relates to the use of the microemulsions of the invention for the preparation of a medicament which can be administered to humans or to animals.

By way of example, the microemulsions based on one of the mixtures of fatty acids described in U.S. Pat No. 5,709,863 may be used in the treatment of anxiety in cats or more generally for modifying the physiological responses in humans or animals.

The examples which follow further illustrate the invention.

EXAMPLE 1

The following compositions, whose formulation is presented in the following tables 1 and 2, are prepared by simply mixing the constituents:

TABLE 1

| Constituents | Formulation 1.1 (parts by weight) | Formulation 1.2 (parts by weight) |
| --- | --- | --- |
| Oleic acid | 3.00 | 4.20 |
| Linoleic acid | 4.20 | 5.25 |
| Palmitic acid | 2.80 | 3.75 |
| Palmitoleic acid | — | 1.80 |
| Diethyl ether of diethylene glycol | — | 20.00 |
| N-Methylpyrrolidone | 20.00 | — |
| PEG-600 oleate | — | 15.00 |
| Sodium lauryl sulphate | 10.00 | — |
| Isopropanol | 10.00 | 15.00 |
| Water | 50.00 | 35.00 |

TABLE 2

| Constituents | Formulation 1.3 (parts by weight) | Formulation 1.4 (parts by weight) |
| --- | --- | --- |
| Fatty acids | 20.00 | 20.00 |
| Isopropanol | 10.00 | 20.00 |
| N-Methylpyrrolidone | 24.75 | 25.70 |
| Polysorbate 80 | 25.00 | 25.00 |
| Preservatives | — | 1.01 |
| Water | 20.25 | 8.29 |

Formulations 1.3 and 1.4 contain more precisely the following proportions of $C_{10}$—$C_{18}$ fatty acids:

| Fatty acids | Formulation 1.3 | Formulation 1.4 |
| --- | --- | --- |
| Linoleic acid | 7.0 | 7.0 |
| Oleic acid | 6.2 | 6.2 |
| Palmitic acid | 4.0 | 4.0 |
| Myristic acid | 1.2 | 1.2 |
| Lauric acid | 1.2 | 1.2 |
| Capric acid | 0.4 | 0.4 |

EXAMPLE 2

In this example, the stability of the compositions of formulations 1.3 and 1.4 of Example 1 was studied.

The compositions tested were kept for 6 months at 25° C.

Another test was carried out, keeping the microemulsions for 3 to 6 months at 40° C.

During the entire duration of the tests, the formulations 1.3 and 1.4 remained clear.

Analysis of the respective content of fatty acids after 6 months shows, moreover, an excellent stability of the compositions at 25° C.

At 40° C., a slight modification of the formulation in relation to the fatty acids is observed after 6 months in the case of composition 1.3:
   the content of linoleic acid is reduced by 6% by weight;
   the content of palmitic acid is reduced by 2% by weight; and the content of myristic acid is reduced by 1% by weight.

At 40° C., a slight modification of the formulation in relation to the fatty acids is observed after 3.5 months in the case of composition 1.4:

the content of linoleic acid is reduced by 2% by weight;
the content of palmitic acid is reduced by 3% by weight;
the content of myristic acid is reduced by 5% by weight.

These results confirm the excellent physical and chemical stability of the microemulsions of the invention.

What is claimed is:

1. Stable, nondetergent composition for administration to humans or animals comprising, in microemulsion form:
    from 5 to 30% by weight of one or more fatty acids with a free carboxylic acid function, as active ingredient;
    from 5 to 35% by weight of one or more surfactants;
    from 5 to 30% by weight of one or more $C_1$–$C_{12}$ alcohols, as cosurfactant;
    from 5 to 35% by weight of one or more water-soluble compounds with a carbonyl or hydroxyl function; and
    from 0 to 35% by weight of one or more water-immiscible compounds;
the composition having a pH of less than 6.5.

2. Composition according to claim 1, characterized in that the active ingredient consists of one or more $C_4$–$C_{22}$ fatty acids with a free carboxylic acid function.

3. Composition according to claim 1, characterized in that the active ingredient consists of one or more fatty acids with a free carboxylic acid function capable of modifying the behavior or the physiological responses of humans or animals.

4. Composition according to claim 1, characterized in that the active ingredient is a pheromone consisting of the one or more fatty acids.

5. Composition according to claim 1, characterized in that the active ingredient comprises oleic acid and palmitic acid.

6. Composition according to claim 1, characterized in that the active ingredient comprises oleic acid and n-butyric acid.

7. Composition according to claim 1, characterized in that the active ingredient comprises palmitic acid, oleic acid, and linoleic acid.

8. Composition according to claim 1, characterized in that the active ingredient comprises palmitic acid, oleic acid, linoleic acid, and myristic acid.

9. Composition according to claim 1, characterized in that the active ingredient comprises palmitic acid, oleic acid, linoleic acid, and palmitoleic acid.

10. Composition according to claim 1, characterized in that the surfactant is one or more anionic or nonionic surfactants.

11. Composition according to claim 10, characterized in that the surfactant is (a) an alkali metal ($C_6$–$C_{18}$) alkyl sulphate, (b) the product of condensation of a $C_8$–$C_{22}$ fatty acid with a $C_2$–$C_3$ alkylene oxide, or (c) the product of condensation of a $C_8$–$C_{22}$ fatty acid ester of sorbitol with a $C_2$–$C_3$ alkylene oxide.

12. Composition according to claim 1, characterized in that the cosurfactant is one or more $C_1$–$C_4$ alkanols.

13. Composition according to claim 12, characterized in that the cosurfactant is ethyl alcohol or isopropyl alcohol.

14. Composition according to claim 1, characterized in that the one or more water-soluble compounds are selected from the group consisting of N-methylacetamide, N,N-dimethylacetamide, N-methylpyrrolidone, a glycol optionally in $C_1$–$C_4$ alkyl monoether form, a monosaccharide, a disaccharide, and glycerol.

15. Composition according to claim 1, characterized in that the one or more water-immiscible compounds are present and are selected from the group consisting of a saturated $C_5$–$C_{16}$ hydrocarbon, a $C_4$–$C_{20}$ fatty acid mono-, di- or triglyceride, and a ($C_4$–$C_{20}$) alkylpyrrolidone.

16. Composition according to claim 1, characterized in that the pH is between 3 and 6.

17. Composition according to claim 1, characterized in that it comprises:
    from 10 to 30% by weight of the one or more fatty acids with a free carboxylic acid function;
    from 10 to 30% by weight of the one or more nonionic or anionic surfactants;
    from 5 to 25% by weight of the one or more $C_1$–$C_{12}$ alcohols; and
    from 10 to 30% by weight of the one or more water-soluble compounds.

18. Composition according to claim 1, characterized in that the one or more surfactants is
    a) an anionic surfactant selected from the group consisting of alkyl sulphates in which the alkyl chain is $C_6$–$C_{18}$, alkyl benzenesulphonates in which the alkyl chain is $C_6$–$C_{18}$, and dialkyl sulphosuccinates in which the alkyl chain is $C_6$–$C_{18}$,
    b) a nonionic surfactant selected from the group consisting of:
        a product of condensation of an aliphatic $C_8$–$C_{22}$ fatty alcohol with a $C_2$–$C_3$ alkylene oxide in which the $C_2$–$C_3$ alkylene oxide is ethylene oxide, propylene oxide, or a mixture of ethylene oxide and propylene oxide;
        a product of condensation of a ($C_8$–$C_{22}$)alkylphenol with a $C_2$–$C_3$ alkylene oxide in which the $C_2$–$C_3$ alkylene oxide is ethylene oxide, propylene oxide, or a mixture of ethylene oxide and propylene oxide;
        a product of condensation of a $C_8$–$C_{22}$ fatty acid with a $C_2$–$C_3$ alkylene oxide in which the $C_2$–$C_3$ alkylene oxide is ethylene oxide, propylene oxide, or a mixture of ethylene oxide and propylene oxide;
        a product of condensation of a $C_8$–$C_{22}$ fatty acid glyceride with a $C_2$–$C_3$ alkylene oxide in which the $C_2$–$C_3$ alkylene oxide is ethylene oxide, propylene oxide, or a mixture of ethylene oxide and propylene oxide;
        a product of condensation of a $C_8$–$C_{22}$ fatty acid ester of sorbitol with a $C_2$–$C_3$ alkylene oxide in which the $C_2$–$C_3$ alkylene oxide is ethylene oxide, propylene oxide, or a mixture of ethylene oxide and propylene oxide;
        a product of condensation of sorbitol with a $C_8$–$C_{22}$ fatty acid; or
    c) a combination of the anionic surfactant and nonionic surfactant.

19. Composition of claim 18, characterized in that the one or more surfactants is
    a) the combination of
        a product of condensation of a $C_8$–$C_{22}$ fatty acid ester of sorbitol with a $C_2$–$C_3$ alkylene oxide in which the $C_2$–$C_3$ alkylene oxide is ethylene oxide, propylene oxide, or a mixture of ethylene oxide and propylene oxide, with
        a product of condensation of sorbitol with a $C_8$–$C_{22}$ fatty acid,
    b) the combination of a dialkyl sulphosuccinate with
        a product of condensation of a $C_8$–$C_{22}$ fatty acid ester of sorbitol with a $C_2$–$C_3$ alkylene oxide in which the $C_2$–$C_3$ alkylene oxide is ethylene oxide, propylene oxide, or a mixture of ethylene oxide and propylene oxide, with a product of condensation of sorbitol with a $C_8$–$C_{22}$ fatty acid, or c) the combination of an alkyl sulphate with
a product of condensation of a $C_8$–$C_{22}$ fatty acid ester of sorbitol with a $C_2$–$C_3$ alkylene oxide in which the $C_2$–$C_3$ alkylene oxide is ethylene oxide, propylene oxide, or a mixture of ethylene oxide and propylene oxide, with
a product of condensation of sorbitol with a $C_8$–$C_{22}$ fatty acid.

20. Stable, nondetergent composition for administration to humans or animals comprising, in microemulsion form:
from 5 to 30% by weight of one or more fatty acids with a free carboxylic acid function, as active ingredient;
from 5 to 35% by weight of one or more surfactants;
from 5 to 30% by weight of one or more $C_1$–$C_{12}$ alcohols, as cosurfactant; and
from 5 to 35% by weight of one or more water-soluble compounds with a carbonyl or hydroxyl function;
the composition having a pH of less than 6.5.

21. Stable, nondetergent composition for administration to humans or animals comprising, in microemulsion form:
from 5 to 30% by weight of one or more fatty acids with a free carboxylic acid function, as active ingredient;
from 5 to 35% by weight of one or more surfactants;
from 5 to 30% by weight of one or more $C_1$–$C_{12}$ alcohols, as cosurfactant;
from 5 to 35% by weight of one or more water-soluble compounds with a carbonyl or hydroxyl function; and
from 8 to 20% by weight of one or more water-immiscible compounds;
the composition having a pH of less than 6.5.

22. Method for modifying the behavior of a human or animal, without a therapeutic or prophylactic treatment being involved, comprising administration of the composition according to claim 1 to the human or animal by bringing the composition into contact with olfactory organs through the inlet of the respiratory tract in the human or animal.

23. Method for modifying the physiological responses in a human or animal comprising administration of the composition according to claim 1 to the human or animal by bringing the composition into contact with olfactory organs through the inlet of the respiratory tract in the human or animal.

24. Method according to claim 22, wherein the contacting takes place via the natural respiratory mechanisms in the human or animal after spraying, nebulization, or atomization of the composition into the environment around the human or animal or after application of the composition in the environment.

* * * * *